United States Patent [19]
Broger et al.

[11] Patent Number: 6,037,479
[45] Date of Patent: Mar. 14, 2000

[54] CHIRAL DIARSINE COMPOUNDS

[75] Inventors: Emil Albin Broger, Magden; Marco Cereghetti, Basel; Frank Kienzle, Flüh, all of Switzerland

[73] Assignee: Hoffman-La Roche Inc., Nytley, N.J.

[21] Appl. No.: 09/105,592

[22] Filed: Jun. 26, 1998

[30] Foreign Application Priority Data

Jul. 2, 1997 [EP] European Pat. Off. .............. 97110940

[51] Int. Cl.[7] ....................................................... A61B 1/00
[52] U.S. Cl. ........................... 549/60; 502/102; 502/153; 502/179; 502/181; 502/185; 502/229; 502/326; 549/460
[58] Field of Search ...................... 549/60, 460; 502/102, 502/153, 179, 181, 185, 229, 326

[56] References Cited

U.S. PATENT DOCUMENTS

| | | |
|---|---|---|
| 4,556,740 | 12/1985 | Hansen et al. . |
| 5,302,738 | 4/1994 | Foricher et al. . |
| 5,448,172 | 9/1995 | Cereghetti et al. . |
| 5,508,438 | 4/1996 | Broger et al. . |

FOREIGN PATENT DOCUMENTS 0 398 132   9/1995   European Pat. Off. .

OTHER PUBLICATIONS

Kojima, et al., Synthesis and Evaluation of a New Chiral Arsine Ligand; 2,2'–bis(diphenylarsino)–1,1'–binaphthyl (BINAs), Tetrahedron Letters, vol. 38, No. 19, pp. 3459–3460 (1997).

Suk Young Cho, et al., Synthesis and Evaluation of a New Chiral Ligand: 2–diphenylarsino–2'–diphenylphosphino–1, 1'–binaphthyl (BINAPAs), Tetrahedron Letters, vol. 39, pp. 1773–1776, 1998.

David W. Allen, et al., Synthesis and Reactions of 2,2'–Biphenylylenebisdiethylphosphine. Formation of Cyclic Diquaternary Dibromides with Alkylene Dibromides, and the Nature and Probable Mechanism of their Thermal Decomposition, J. Chem. Soc., Section C: Organic Chemistry, pp. 1869–1875 (1967).

Engelhardt, et al., Axially Asymmetric Metal Alkyls. Part 6. [1] Lithiation of 2,2'–Dimethyl–1,1'–binaphthyl and its Trimethylsilylated Compounds, and of 2,2',6,6'–Tetramethyl–1, 1'–biphenyl(Asymmetric Induction): X–Ray Crystal Structures of Monomeric [{Li(Me$_2$NCH$_2$CH$_2$NME$_2$)}$_2$(2–CH$_2$C$_{10}$H$_2$)$_2$}] and Li{(Me$_2$NCH$_2$CH$_2$)$_2$NMe}–{2–CH$_2$–6–Me(C$_6$H$_2$)$_2$–2', 6'–Me$_2$}], J. Chem. Soc. Dalton Trans, pp. 2403–2409 (1988).

Kagan, Chiral Ligands for Asymmetric Catalysis in Asymmetric Synthesis, vol. 5,. J.D. Morrison ed., pp. 1–39 (Academic Press 1985).

Kojima, et al., Synthesis and Evaluation of a New Chiral Arsine Ligand; 2,2'–bis(diphenylarsino)–1,1'–binaphthyl (BINAs), Tetrahedron Letters, vol. 38, No. 19, pp. 3459–3460 (1997).

Wild, Optically active arsines: preparation, uses and chiroptical properties, ch.3, pp. 88–153, (Wiley 1994).

Mar., Advanced Organic Chemistry, 3d ed, pp. 89–90, (Wiley 1985).

Attwood, et al., Synthesis of the Potent Potassium Channel Opener Ro 31–6930 Via Claisen Rearrangement and Tandem Regiocontrolled Cyclisation, Tetrahedron Letters, vol. 32, No. 6, pp. 811–814 (1991).

Attwood, et al., Synthesis of Homochiral Potassium Channel Openers: Role of the Benzopyranyl 3–Hydroxyl Group in Chromakalim and Pyridine N–oxides in determining the Biological Activities of Enantiomers, Bioorganic & Medicinal Chemistry Letters, vol. 2, No. 3, pp. 229–234, (1992).

Houben–Weyl, Methoden der Organischen Chemie, vol. 13/8: Metallorganische Verbindungen As, Sb, Bi, Georg Thiem Verlag Stuttgart, pp. 232–254 (1978).

*Primary Examiner*—Johann Richter
*Assistant Examiner*—Taofiq A. Solola
*Attorney, Agent, or Firm*—George W. Johnston; William H. Epstein; Lewis J. Kreisler

[57] ABSTRACT

Novel, chiral diarsine compounds, which are present in the (R)- or (S)- or (rac)-form, of the formula

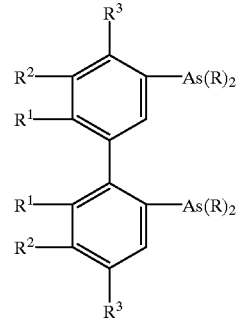

I wherein

R signifies an optionally substituted aryl from the group of phenyl, naphthyl, furyl and thienyl; $C_{3-8}$-cycloalkyl or $C_{1-8}$-alkyl;

$R^1$, $R^2$, $R^3$ each independently signify $C_{1-8}$-alkyl, $C_{1-8}$-alkoxy, aryloxy, F or Cl, $R^2$ and $R^3$ each independently also signify hydrogen or $R^1$ and $R^2$ together signify tetramethylene or a benzo or benzofuro system or dioxymethylene on the respective benzene ring; or $R^2$ and $R^3$ together signify dioxymethylene, and the manufacture of the diarsine compounds of formula I, as well as complexes of the compounds of formula I with Group VIII metal and their use for enantioselective reactions.

70 Claims, No Drawings

6,037,479

CHIRAL DIARSINE COMPOUNDS

BACKGROUND OF THE INVENTION

Among the known arsine compounds only a few chiral compounds which are useful as ligands in metal-catalyzed asymmetric reactions are known (H. B. Kagan, Asymmetric Synthesis, Vol 5, Ed. J. D. Morrison, Academic Press). When these known arsine compounds are used in metal complexes for asymmetric reactions the optical yields lie in the region of 27% to 39%.

U.S. Pat. Nos. 4,556,740 and 5,508,438 disclose certain chiral phosphorus compounds as well as complexes of such compounds with Group VIII metals for use as catalysts for asymmetric hydrogenations and enantioselective hydrogen displacements in prochiral allylic systems. U.S. Pat. No. 5,302,738 discloses certain chiral phosphine compounds.

The chiral arsine ligand 2,2'-bis(diphenylarsino)-1,1'-binaphthyl is described in A. Kojima et al., Tetrahedron Letters (May 1997) 38(19): 3459–3460.

Certain optically active arsine compounds are disclosed in S. B. Wild, "Optically active arsines: preparation, uses and chiroptical properties" in The Chemistry of Organic Arsenic, Antimony and Bismuth Compounds, S. Patai ed. (Wiley 1994) ch.3, pages 90–152.

SUMMARY OF THE INVENTION

The present invention is concerned with novel, chiral diarsine compounds, which are present in the (R)- or (S)-form or as a racemate, of the formula

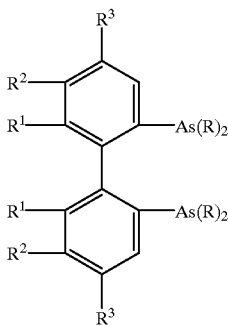

I wherein

R signifies an optionally substituted aryl from the group of phenyl, naphthyl, furyl and thienyl; $C_{3-8}$-cycloalkyl or $C_{1-8}$-alkyl;

$R^1$, $R^2$, $R^3$ each independently signify $C_{1-8}$-alkyl, $C_{1-8}$-alkoxy, aryloxy, F or Cl, $R^2$ and $R^3$ each independently also signify hydrogen or $R^1$ and $R^2$ together signify tetramethylene or a benzo or benzofuro system, or dioxymethylene on the respective benzene ring, or $R^2$ and $R^3$ together signify dioxymethylene.

Rotation about the central bond of these biphenyl compounds is restricted by the four groups at the ortho positions of the phenyl rings, so that compounds of formula I can be present in two different stereoisomeric forms called atropisomers (see March, Advanced Organic Chemistry, 3d ed. 1985, Wiley, pages 89–90).

The invention is also concerned with the manufacture of the diarsine compounds of general formula I as well as complexes of optically active compounds of formula I with Group VIII metals and their use for enantioselective reactions, such as e.g. asymmetric hydrogenations, enantioselective hydrogen displacements, and the like.

The object of the present invention is to provide novel chiral diarsine compounds which, moreover, are useful in enantioselective reactions and which give rise to improved optical yields.

The object is achieved by the atropisomeric diarsine compounds of formula I in accordance with the invention.

DETAILED DESCRIPTION OF THE INVENTION

The term "$C_{1-8}$-alkyl" signifies in the scope of the present invention straight-chain or branched alkyl groups with 1–8 carbon atoms, such as e.g. methyl, ethyl, propyl, isopropyl, butyl, isobutyl, tert.butyl, pentyl, isopentyl, neopentyl, hexyl, isohexyl, heptyl or octyl. The term "$C_{1-8}$-alkoxy" signifies ether groups in which the alkyl residue is as defined above.

The term "$C_{3-8}$cycloalkyl" signifies in the scope of the present invention 3–8-membered rings, such as e.g. cyclopropyl, cyclobutyl, cyclopentyl, cyclohexyl, cycloheptyl and cyclooctyl, which can be optionally substituted with alkyl, alkoxy or aryl groups.

The term "optionally substituted aryl" signifies in the scope of the present invention phenyl, naphthyl, furyl and thienyl residues, which can be unsubstituted or mono- or poly-substituted. As substituents there come into consideration e.g. phenyl, $C_{1-8}$-alkyl, $C_{1-8}$-alkoxy and di-$C_{1-6}$-alkylamino groups as well as halogen atoms.

The term "aryloxy" signifies ether groups in which aryl is optionally substituted aryl as defined above.

The term "benzo or benzofuro system" denotes the residues

and, respectively,

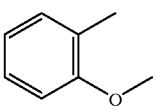

which are unsubstituted or substituted by $C_{1-8}$-alkyl, $C_{1-8}$-alkoxy or phenyl.

Diarsine compounds in which $R^1$ is methyl or methoxy, $R^2$ and $R^3$ are hydrogen and R is phenyl or $R^1$ and $R^2$ together are benzo and $R^3$ is hydrogen are especially preferred. Particularly preferred are optically active compounds of formula I, such as, for example (R) or (S)-(6,6'-dimethylbiphenyl-2,2'-diyl)bis(diphenylarsine)

(R) or (S)-(6,6'-dimethylbiphenyl-2,2'-diyl)bis(dicyclohexylarsine)

(R) or (S)-(6,6'-dimethylbiphenyl-2,2'-diyl)bis(di-p-tolylarsine).

The process for the manufacture of the diarsine compounds of general formula I in accordance with the invention comprises reacting a racemic or optically active compound of formula III

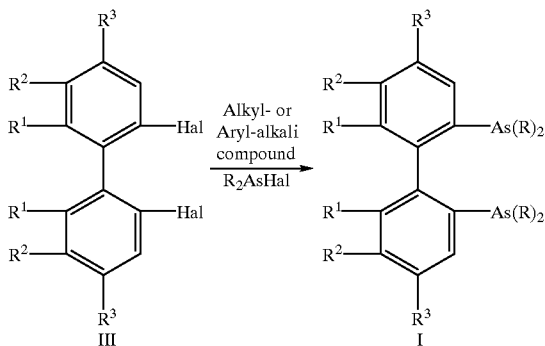

wherein $R^1$, $R^2$ and $R^3$ have the above significance, with a compound of the formula $R_2AsHal$, wherein R has the significance given above and Hal signifies bromine or iodine, in the presence of an alkali-alkyl or alkali-aryl compound.

As used herein the term "alkali" means the alkali metals lithium, sodium and potassium, with lithium being preferred.

The molar ratio of the alkali-alkyl or alkali-aryl compound to the compound of formula III is preferably at least 2 to 1, more preferably about 2.3 to 1.

As solvents there are used aliphatic hydrocarbons such as pentane, hexane, heptane, octane and isomers thereof; or aromatic hydrocarbons such as benzene, toluene, xylene or the like; and/or ethers such as dimethyl ether, diethyl ether, diisopropyl ether, tetrahydrofuran or the like. Mixtures of aromatics and ethers such as e.g. toluene/diethyl ether are preferably used.

The compounds of formula III can be prepared as described in U.S. Pat. No. 4,556,740.

The compounds $R_2AsHal$ are known compounds or analogues of known compounds, which can be prepared in a manner known per se (e.g. Houben-Weyl, Methoden der Organischen Chemie, volume 13/8: Metallorganische Verbindungen As, Sb, Bi; Georg Thieme Verlag Stuttgart, 1978).

The resolution of a compound of formula I which is present in racemic form into its optically active isomers can be carried out by techniques known in the art, for example as described in S. B. Wild in The Chemistry of Organic Arsenic, Antimony and Bismuth Compounds, S. Patai ed. (Wiley 1994) ch. 3, pages 95–122, or analogously thereto.

The thus-obtained adducts of the compounds of formula I with (−)- or (+)-DBT or DTT can subsequently be treated with an inorganic base in an analogous manner to phosphine oxide adducts, wherein the respective (R) or (S) form of the compounds of formula I is liberated.

The atropisomeric diarsine compounds of formula I in accordance with the invention form complexes with transition metals of Group VIII, e.g. with ruthenium, rhodium and iridium, which are useful as catalysts in asymmetric hydrogenations and also for enantioselective hydrogen displacements.

Rhodium and ruthenium complexes are preferred for the mentioned hydrogenations. These catalysts, i.e. the complexes from a Group VIII metal and the diarsine compounds of formula I, are novel and are also an object of the present invention.

Examples of such optically active metal complexes are especially optically active cationic and neutral rhodium and ruthenium complexes of general formula IIa to IIe

| | |
|---|---|
| $[Rh(Y)(L_n)]^+A^-$ | II-a |
| $[Rh(Y)(L_n)B]$ | II-b |
| $[Ru(Y)]^{2+}(A^-)_2$ | II-c |
| $[Ru(Y)(B)_2]$ | II-d |
| $[Ru(Y)(C^1)(C^2)_{2-m}](C^3)_m$ | II-e | wherein
L signifies a neutral ligand,
$A^-$ signifies the anion of an oxygen acid or complex acid,
B signifies an anionic coordinating ligand,
$C^1$ signifies benzene, p-cymene, xylene or hexamethylbenzene,
$C^2$ signifies halogen,
$C^3$ signifies halogen or $A^-$,
n signifies 0, 1 or 2,
m signifies 0, 1 or 2 and
Y signifies a chiral atropisomeric diarsine compound of formula I.

In accordance with this invention "B" can be any conventional anionic coordinating ligand. Examples of such anionic coordinating ligands include halogen, a carboxylic acid residue, a sulphonate residue such as e.g. tosylate or methanesulphonate, a 1,3-diketonate such as e.g. acetylacetonate, an optionally substituted phenolate, hydroxy, nitrate, nitrite, cyanate, rhodanide, cyanide, allyl and 2-methylallyl.

The term "neutral ligand" signifies in the scope of the present invention any exchangeable ligand, e.g. an olefin such as ethylene, propylene, cyclooctene, 1,5-hexadiene, norbornadiene, 1,5-cyclooctadiene, and the like, a nitrile such as acetonitrile or benzonitrile, or also the solvent which is used. This ligand can be exchanged in the hydrogenation. Where more than one such ligand is present, these can also be different from one another.

The term "oxygen acid or complex acid" signifies in the scope of the present invention acids from the group of $H_2SO_4$, $HClO_4$, $HBrO_4$, $HIO_4$, $HNO_3$, $H_3PO_4$, $H_3PO_3$ and $CF_3SO_3H$ as well as halogen complexes with the elements boron, phosphorus, arsenic, antimony or bismuth. Preferred representatives are $HClO_4$, $CF_3SO_3H$, $HPF_6$, $HBF_4$, $HB(Ph)_4$, $HB(3,5(CF_3)_2\text{-}C_6H_3)_4$, $HSbF_6$ and $HAsF_6$.

The term "halogen" embraces fluorine, chlorine, bromine and iodine.

The complexes from a Group VIII metal and a compound of formula I, such as e.g. the complexes of formulae II-a to II-e, can be produced analogously to corresponding diphosphine ligands in a manner known per se, for example as described in U.S. Pat. No. 5,488,172, issued Jan. 30, 1996 or U.S. Pat. No. 5,508,438, issued Apr. 16, 1996.

For example, the aforementioned complexes can be manufactured by reacting a compound of formula I with a compound which can yield a metal of Group VIII, in a suitable, inert organic or aqueous solvent. Examples of compounds which yield rhodium include organic rhodium complexes with ethylene, propylene and the like, as well as with bis-olefins, e.g. (Z,Z)-1,5-cyclooctadiene, 1,5-hexadiene, bicyclo[2.2.1]hepta-2,5-diene or with other dienes which form readily soluble complexes with rhodium. Preferred -compounds which yield rhodium are di-μ-chloro-bis[η⁴-(Z,Z)-1,5-cyclooctadiene]dirhodium(I), di-μ-chloro-bis[η⁴-norbornadiene]dirhodium(I), di-μ-perfluoroacetato-bis-[η⁴-(Z,Z)-1,5-cyclooctadiene]dirhodium(I), bis[η⁴-(Z,Z)-1,5-cyclooctadiene]-rhodium tetrafluoroborate or bis[-η⁴-(Z,Z)-cyclooctadiene]rhodium perchlorate.

For the performance of asymmetric hydrogenations and hydrogen displacements, optically active atropisomeric compounds of formula I can be brought into contact as such, in a solution of a compound to be treated, with a compound which yields a metal of Group VIII. Alternatively, the optically active atropisomeric compounds of formula I can be firstly reacted in a suitable solvent with a compound which yields a metal of Group VIII to give the corresponding catalyst complex and this can then be added to a solution of the compound to be treated. The latter method is preferred.

Not only the reaction of the compounds of formula I with a compound which yields a metal of Group VIII, but also the aforementioned asymmetric hydrogenations and hydrogen displacements can be carried out in suitable organic solvents which are inert under the reaction conditions. In particular, lower alcohols, halogenated hydrocarbons or mixture of the aforementioned solvents with ethers or mixtures of alcohols with esters or with ketones are used as such solvents.

The molar ratio substrate/catalyst (S/C) between the compounds to be treated and the Group VIII metal complex catalyst conveniently lies between 20 to 30000, preferably between 100 to 6000.

The aforementioned asymmetric hydrogenations and hydrogen displacements are conveniently carried out at temperatures in the range of about 0° C. to 150° C., preferably 10 to 100° C., particularly in the temperature range of about 20° C. to 80° C., and a pressure of about 1 to 200 bar, preferably 1 to 150 bar and particularly 10 to 80 bar.

The complexes in accordance with the invention with compounds of formula I are suitable, for example, for the asymmetric hydrogenation of chromenylpyridine derivatives of formula IV to compounds of formula V

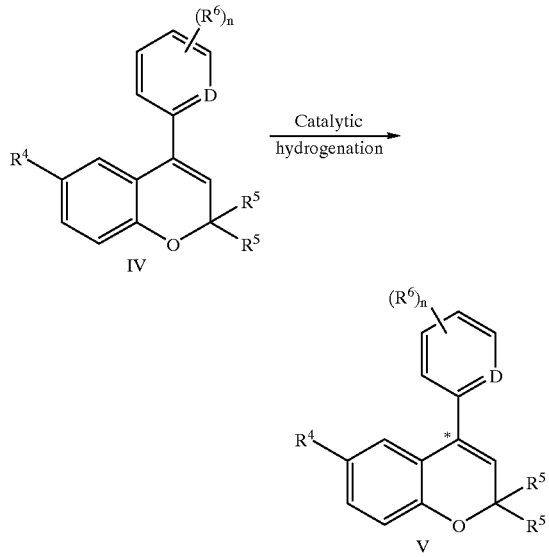

wherein

D is N or N-oxide, $R^4$ is hydrogen, cyano, halogen, nitro, trifluoromethyl, $C_{1-8}$-alkyl, $C_{1-8}$-alkoxycarbonyl, $C_{1-8}$-alkylthio, $C_{1-8}$-alkylsulphonyl, aroyl, carbamoyl, mono($C_{1-8}$-alkyl)carbamoyl, di($C_{1-8}$-alkyl)carbamoyl or $C_{1-8}$-alkanoyl, $R^5$ is hydrogen, $C_{1-8}$-alkyl or $CH_2F$, $R^6$ is $C_{1-8}$-alkyl, halogen, amino, $CO_2$-($C_{1-8}$alkyl), $C_{1-8}$-alkoxy, hydroxy, phenyl, tolyl or in the case of n=2 a benzo residue and n is 0, 1 or 2 which is effected in suitable organic solvents which are inert under the reaction conditions. In particular, lower alcohols, halogenated hydrocarbons or mixture of the aforementioned solvents with ethers or mixtures of alcohols with esters or with ketones are used as such solvents.

The term "aroyl" signifies benzoyl optionally substituted by a halogen or nitro substituent and the term "aryl" signifies phenyl or naphthyl optionally substituted by one or more halogen, cyano or $C_{1-8}$-alkyl substituents.

Esters, hydrocarbons, ethers or mixtures thereof are preferred solvents for the hydrogenation of the chromenylpyridine N-oxides.

The compounds of formula IV include potassium channel blockers. The preparation of compounds of formula IV in which D is N is described in Attwood et al., Tetrahedron Lett.(1991) 32(6): 811–814. The preparation of compounds of formula IV in which D is N-oxide is described in Attwood et al., Bioorg. Med. Chem. Lett. (1992) 2(3): 229–234.

The asymmetric hydrogenation of chromenylpyridine N-oxides of formula IV is preferably carried out in the presence of rhodium complexes with the compounds of formula I, e.g. in the presence of rhodium complexes of the formulae $$[Rh(Y)(L_n)]^+A^- \qquad \text{II-a}$$

and $$[Rh(Y)(L_n)B] \qquad \text{II-b.}$$

The asymmetric hydrogenation of chromenylpyridines of formula IV is preferably carried out in the presence of ruthenium complexes with the compounds of formula I, e.g. in the presence of ruthenium complexes of the formulae $$[Ru(Y)]^{2+}(A^-)_2 \qquad \text{II-c}$$

$$[Ru(Y)(B)2] \qquad \text{II-d}$$

and $$[Ru(Y)(C^1)(C^2)_{2-m}](C^3)_m \qquad \text{II-e.}$$

Especially suitable solvents for the hydrogenation of the chromenylpyridines are chlorinated hydrocarbons, alcohols or mixtures thereof.

The hydrogenation of compounds of formula IV is conveniently carried out at temperatures in the range of about 0° C. to 150° C., preferably 10° C. to 100° C., particularly in the temperature range of about 20° C. to 80° C., and a pressure of about 1 to 200 bar, preferably 1 to 150 bar and particularly 10 to 80 bar.

The molar ratio substrate/catalyst (S/C) between the compounds of formula IV to be hydrogenated and the metal complex catalysts of formulae II-a to II-e conveniently lies between 20 to 30000, preferably between 100 to 6000.

The following Examples illustrate the invention and do not in any manner represent a limitation. In the Examples the selected terms have the following significance:

HPLC High pressure liquid chromatography e.e. Enantiomeric excess

RT Room temperature m.p. Melting point (R)-BIPHAS (R)-6,6'-Dimethyl-biphenyl-2,2'-diyl-bis(diphenylarsine)

(S)-p-Tol-BIPHAS (S)-6,6'-Dimethyl-biphenyl-2,2'diyl-bis(di-p-tolylarsine)

(Rh(COD)$_2$BF$_4$ Bis-(cycloocta-1,5-diene)rhodium(I) tetrafluoroborate

All temperatures are given in °Celsius.

EXAMPLE 1

(R)-(6,6'-Dimethylbiphenyl-2,2'-diyl)bis (diphenylarsine)

91.8 g (0.40 mol) of diphenylarsine in 250 ml of dry tetrahydrofuran were placed in a 3 l flask having a magnetic stirrer, dropping funnel and nitrogen gasification. A solution of 62 g (0.244 mol) of iodine in 100 ml of dry tetrahydrofuran was added dropwise within 15 min. while cooling with an ice bath. After an additional stirring period of 15 min. the solution was evaporated and the residue was taken up in 50 ml of dry tetrahydrofuran.

30.0 g (69.1 mmol) of (R)-2,2'-diiodo-6,6'-dimethylbiphenyl in 600 ml of dry toluene and 100 ml of ether were placed in a 2.5 l sulphonation flask having a magnetic stirrer, intensive condenser, dropping funnel, thermometer and nitrogen gasification. 100 ml of 1.6N butyllithium solution in hexane (160 mmol) were added dropwise at −70° to −55° and the mixture was stirred at −60° for a further 15 min. Subsequently, the tetrahydrofuran solution of iododiphenylarsine obtained above was added dropwise at −50°. After stirring at RT overnight the mixture was treated with 250 ml of water, stirred for 30 min. and diluted with 500 ml of ethyl acetate. The organic phase was separated, washed neutral with water, dried over Na$_2$SO$_4$, filtered and the filtrate was evaporated. The residue (151.6) was chromatographed on 500 g of silica gel (elution hexane/toluene 0% ? 10%). 13.0 g (29%) of (R)-(6,6'-dimethylbiphenyl-2, 2'-diyl)bis(diphenylarsine) were isolated as a white powder. For analysis, it was recrystallized from 10 ml of ethyl acetate. There were obtained 7.8 g (17%) of (R)-(6,6'-dimethylbiphenyl-2,2'-diyl)bis(diphenylarsine) of m.p. 184–185°; [a]$_D^{20}$=−108° (c=1%, CHCl$_3$). Microanalysis: C$_{38}$H$_{32}$As$_2$ (638.5); calc: C 71.48, H 5.05; found: C 71.67, H 5.38%.

EXAMPLE 2

(rac)-(6,6'-Dimethylbiphenyl-2,2'-diyl)bis(diphenylarsine was prepared in an analogous manner to Example 1 from (rac)-2,2'-diiodo-6,6'-dimethylbiphenyl; m.p. 209–210°.

EXAMPLE 3

(rac)-(6,6'-Dimethoxybiphenyl-2,2'-diyl)-bis-(diphenylarsine) was prepared in an analogous manner to Example 1 from (rac)-2,2'-diiodo-6,6'-dimethoxybiphenyl.

EXAMPLE 4

(R)-(6,6'-Dimethylbiphenyl-2,2'-diyl)bis (dicyclohexylarsine)

13.0 g (30.0 mmol) of (R)-2,2'-diiodo-6,6'-dimethylbiphenyl were placed n 300 ml of dry toluene and 50 ml of ether in a 1.5 l sulphonation flask having a thermometer, dropping funnel and intensive condenser. 44 ml of 1.6N butyllithium solution in hexane (70 mmol) were added dropwise at −70° within 15 min. and the mixture was stirred at −70° for a further 30 min. Then, 38.7 g (120 mmol) of bromodicyclohexylarsine in 80 ml of toluene were added dropwise within 20 min. After stirring at 60° (2 hours) and at RT overnight a solution of 2.60 g (102 mmol) of iodine in 30 ml of tetrahydrofuran was added dropwise, the mixture was stirred for 15 min., treated with 100 ml of water and with 150 ml of IN sodium hydroxide solution and stirred for 30 min. After the addition of 500 ml of ethyl acetate the organic phase was separated, washed neutral with water, dried over Na$_2$SO4, filtered and the filtrate was evaporated. Chromatographic separation of the residue (32 g) on silica gel (600 g, eluant hexane/toluene 0% ® 20%) yielded 8.0 g (40%) of (R)-6,6'-dimethylbiphenyl-2,2'-diyl)bis (dicyclohexylarsine). The analytical sample was recrystallized from CH$_2$Cl$_2$/ethyl acetate 1:1; m.p. 199.5–200.5°; [a]$_D^{20}$=−102.7° (c=1%, CHCl$_3$). Microanalysis: C$_{38}$H$_{56}$As$_2$ (662.71); calc.: C 68.87, H 8.52; found.: C 68.78, H 8.42%.

EXAMPLE 5

(R)- or (S)-(6,6'-Dimethoxybiphenyl-2,2'-diyl)-bis-(dicyclohexylarsine) was prepared in an analogous manner to Example 4 from (R)- or (S)-2,2'-diiodo-6,6'-dimethoxybiphenyl.

EXAMPLE 6

(S)-(6,6'-Dimethylbiphenyl-2,2'-diyl)bis(di-p-tolylarsine)

A reaction carried out in analogy to Example 1 of di-p-tolylarsine [prepared from 42.5 g (122 mmol) of tri-p-tolylarsine] and 17.0 g (40 mmol) of (S)-2,2'-diiodo-6,6'-dimethylbiphenyl yielded 47.5 g of a product mixture. This was chromatographed on 600 g of silica gel (elution hexane/toluene 0% ® 10%) and gave 9.9 g (36%) of (S)-(6,6'-dimethylbiphenyl-2,2'-diyl)bis(di-p-tolylarsine). The analytical sample was recrystallized from ethyl acetate/methanol; m.p. 216–217°; [a]$_D^{20}$=+107.9° (c=1%, CHCl$_3$). Microanalysis: C$_{42}$H$_{40}$As$_2$ (694.63); calc.: C 72.62, H 5.80; found: C 72.79, H 5.96%.

EXAMPLE 7

(R)- or (S)-(6,6'-Dimethoxybiphenyl-2,2'-diyl)-bis-(di-p-tolylarsine) was prepared in an analogous manner to Example 6 from (R)- or (S)-2,2'-diiodo-6,6'-dimethoxybiphenyl.

EXAMPLE 8

(rac)-(6,6'-Dimethylbiphenyl-2,2'-diyl)bis (diphenylarsine)

A solution of 10.0 g (38 mmol) of diphenylarsenic acid in 50 ml of toluene and 50 ml of thionyl chloride was boiled under reflux for 4 h. After cooling the reaction solution was evaporated and the residue was taken up in 50 ml of toluene.

5.2 g (12 mmol) of (R,S)-2-2'-diiodo-6,6'-dimethylbiphenyl were placed in 80 ml of toluene and 20 ml of ether in a 750 ml sulphonation flask having a magnetic stirrer, condenser, dropping funnel, thermometer and N$_2$ gasification. 17 ml of 1.6N butyllithium solution in hexane (27 mmol) were added dropwise at −70° within 3 min. and the mixture was stirred at −70° for a further hour. Subsequently, the toluene solution obtained above was added dropwise at −70°. After stirring at room temperature overnight the solution was treated with 100 ml of water and 10 ml of 3N NaOH, stirred for one hour, the phases were separated and the aqueous phase was extracted with 500 ml of toluene. The combined organic phases were washed neutral with water, dried over Na$_2$SO$_4$, filtered and the filtrate was evaporated. The residue (5.8 g) was chromatographed on 300 g of silica gel. 1.0 g (13%) of (rac)-(6,6'-dimethylbiphenyl-2,2'-diyl)bis(diphenylarsine) was eluted with hexane/toluene 0%→20%. An analytical sample was recrystallized from ethyl acetate; microanalysis: $C_{38}H_{32}As$ (638.52); calc.: C 71.48, H 5.05; found.: C 71.06, H 5.24%.

EXAMPLE 9

(R)-2-(6-Cyano-3,4-dihydro-2,2-dimethyl-2H-1-benzopyran-4-yl)pyridine 1-oxide 100 mg (359 mmol) of 2-(6-cyano-2,2-dimethyl-2H-1-benzopyran-4-yl)pyridine 1-oxide, 9 ml of toluene, 1 ml of dichloromethane, 5.8 mg (14.4 mmol) of $[Rh(COD)_2]BF_4$ and 6.1 mg (14,4 mmol) of (R)-BIPHAS were placed in a 30 ml autoclave in a glove box ($O_2$ content <1 ppm). The autoclave was sealed and the hydrogenation was carried out at 40° while stirring and a pressure of 40 bar. The hydrogenation was interrupted after 20 h. In order to determine the e.e. value and the conversion, a sample of the hydrogenation solution was evaporated and analyzed by HPLC on a chiral phase (Chiralcel OD-H). (R)-2-(6-Cyano-3,4-dihydro-2,2-dimethyl-2H-1-benzopyran-4yl)-pyridine 1-oxide was obtained in quantitative yield: e.e.=85%; chem. purity >99%.

EXAMPLE 10

(S)-2-(6-Cyano-3,4-dihydro-2,2-dimethyl-2H-1-benzopyran-4-yl)pyridine 1-oxide

The hydrogenation with (S)-p-Tol-BIPHAS was carried out in an analogous manner to Example 9. (S)-2-(6-Cyano-3,4-dihydro-2,2-dimethyl-2H-1-benzopyran-4-yl)pyridine 1-oxide was obtained in quantitative yield: e.e=88%; chem. purity >99%.

What is claimed is:

1. A compound, in racemic or (R)- or (S)-form, of the formula

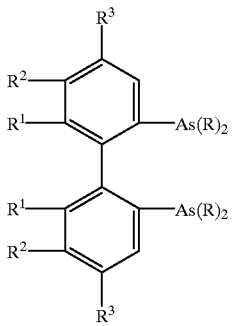

wherein
R is phenyl, naphthyl, furyl or thienyl, unsubstituted or substituted by one or more groups selected from phenyl, $C_{1-8}$alkyl, $C_{1-8}$-alkoxy, di- $C_{1-6}$-alkylamino, and halogen; or $C_{3-8}$-cycloalkyl or $C_{1-8}$-alkyl; and
$R^3$ is $C_{1-8}$-alkyl, $C_{1-8}$-alkoxy, aryloxy, F, Cl, or hydrogen; and
$R^1$ is $C_{1-8}$-alkyl, $C_{1-8}$-alkoxy, aryloxy, F, Cl; and
$R^2$ is $C_{1-8}$-alkyl, $C_{1-8}$-alkoxy, aryloxy, F, Cl or hydrogen; or
$R^1$ and $R^2$ together are tetramethylene, or benzofuro.

2. The compound of claim 1, wherein the compound is in the (R)-form.

3. The compound of claim 1, wherein the compound is in the (S)-form.
4. The compound of claim 1, wherein $R^1$ is $C_{1-8}$-alkyl.
5. The compound of claim 4, wherein $R^1$ is methyl.
6. The compound of claim 1, wherein $R^1$ is $C_{1-8}$-alkoxy.
7. The compound of claim 6, wherein $R^1$ is methoxy.
8. The compound of claim 1, wherein $R^2$ is hydrogen.
9. The compound of claim 1, wherein $R^3$ is hydrogen.
10. The compound of claim 1, wherein $R^2$ and $R^3$ are each hydrogen.
11. The compound of claim 1, wherein R is unsubstituted phenyl.
12. The compound of claim 1, wherein R is $C_{3-8}$-cycloalkyl.
13. The compound of claim 12, wherein R is cyclohexyl.
14. The compound of claim 1, wherein R is phenyl substituted by $C_{1-8}$-alkyl.
15. The compound of claim 14, wherein R is phenyl para-substituted by $C_{1-8}$-alkyl.
16. The compound of claim 15, wherein R is para-tolyl.
17. The compound of claim 1, wherein $R^1$ and $R^2$ together are benzofuro.
18. The compound of claim 1, wherein $R^1$ is $C_{1-8}$-alkyl; $R^2$ and $R^3$ are each hydrogen; and R is unsubstituted phenyl, phenyl substituted by $C_{1-8}$-alkyl, or $C_{3-8}$-cycloalkyl.
19. The compound of claim 18, wherein $R^1$ is methyl.
20. The compound of claim 18, wherein R is unsubstituted phenyl.
21. The compound of claim 18, wherein R is phenyl para-substituted by $C_{1-8}$-alkyl.
22. The compound of claim 21, wherein R is para-tolyl.
23. The compound of claim 18, wherein R is $C_{3-8}$-cycloalkyl.
24. The compound of claim 23, wherein R is cyclohexyl.
25. The compound of claim 1, wherein $R^1$ is $C_{1-8}$-alkoxy; $R^2$ and $R^3$ are each hydrogen; and R is unsubstituted phenyl, phenyl substituted by $C_{1-8}$-alkyl, or $C_{3-8}$-cycloalkyl.
26. The compound of claim 25, wherein $R^1$ is methoxy.
27. The compound of claim 25, wherein R is unsubstituted phenyl.
28. The compound of claim 25, wherein R is phenyl para-substituted by $C_{1-8}$-alkyl.
29. The compound of claim 25, wherein R is para-tolyl.
30. The compound of claim 25, wherein R is $C_{3-8}$-cycloalkyl.
31. The compound of claim 30, wherein R is cyclohexyl.
32. The compound of claim 1, wherein $R^1$ is methyl; $R^2$ and $R^3$ are each hydrogen; and R is unsubstituted phenyl, phenyl substituted by $C_{1-8}$-alkyl, or $C_{3-8}$-cycloalkyl.
33. The compound of claim 32, wherein the compound is (R)- or (S)-(6,6'-Dimethylbiphenyl-2,2'-diyl)-bis-(diphenylarsine).
34. The compound of claim 32, wherein R is phenyl para-substituted by $C_{1-8}$-alkyl.
35. The compound of claim 34, wherein the compound is (R)- or (S)-(6,6'-Dimethylbiphenyl-2,2'-diyl)-bis-di-p-tolylarsine).
36. The compound of claim 32, wherein R is $C_{3-8}$-cycloalkyl.
37. The compound of claim 36, wherein the compound is (R)- or (S)-(6,6'-Dimethylbiphenyl-2,2'-diyl)-bis-(dicyclohexylarsine).
38. The compound of claim 1, wherein $R^1$ is methoxy; $R^2$ and $R^3$ are each hydrogen; and R is unsubstituted phenyl, phenyl substituted by $C_{1-8}$-alkyl, or $C_{3-8}$-cycloalkyl.
39. The compound of claim 38, wherein the compound is (R)- or (S)-(6,6'-Dimethoxybiphenyl-2,2'-diyl)-bis-(diphenylarsine).

40. The compound of claim 38, wherein R is phenyl para-substituted by $C_{1-8}$-alkyl.

41. The compound of claim 40, wherein the compound is (R)- or (S)-(6,6'-Dimethoxybiphenyl-2,2'-diyl)-bis-(di-p-tolylarsine).

42. The compound of claim 38, wherein R is $C_{3-8}$-cycloalkyl.

43. The compound of claim 42, wherein the compound is (R)- or (S)-(6,6'-Dimethoxybiphenyl-2,2'-diyl)-bis-(dicyclohexylarsine).

44. The compound of claim 1, wherein $R^1$ and $R^2$ together are benzofuro; and $R^3$ is hydrogen.

45. A Group VIII metal complex with a compound in optically active (R)- or (S)-form, wherein the compound is of the formula

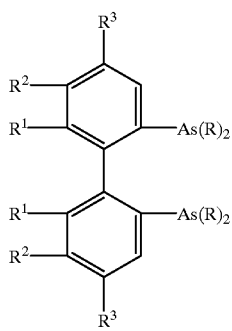

I wherein

R is phenyl, naphthyl, furyl or thienyl, unsubstituted or substituted by one or more groups selected from phenyl, $C_{1-8}$-alkyl, $C_{1-8}$-alkoxy, di- $C_{1-6}$-alkylamino, and halogen; or $C_{3-8}$-cycloalkyl or $C_{1-8}$-alkyl; and $R^3$ is $C_{1-8}$-alkyl, $C_{1-8}$-alkoxy, aryloxy, F, Cl, or hydrogen; and $R^1$ is $C_{1-8}$-alkyl, $C_{1-8}$-alkoxy, aryloxy, F, or Cl; and $R^2$ is $C_{1-8}$-alkyl, $C_{1-8}$-alkoxy, aryloxy, F, Cl or hydrogen; or $R^1$ and $R^2$ together are tetramethylene, benzo, or benzofuro.

46. The complex of claim 45, wherein $R^1$ and $R^2$ together are tetramethylene or benzofuro.

47. The complex of claim 45, wherein the Group VIII metal is ruthenium.

48. The complex of claim 47 of the formula

[Ru(Y)]²⁺(A⁻)₂ wherein

Y is the optically active compound of formula I; and

A⁻ is the anion of an oxygen acid or complex acid.

49. The complex of claim 47 of the formula

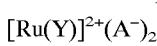

wherein

Y is the optically active compound of formula I; and
B is an anionic coordinating ligand.

50. The complex of claim 47 of the formula

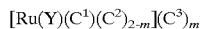

wherein

Y is the optically active compound of formula I;

$C^1$ is benzene, p-cymene, xylene or hexamethylbenzene;

$C^2$ is a halogen;

$C^3$ is a halogen or the anion of an oxygen acid or complex acid; and m is 0, 1 or 2.

51. The complex of claim 45, wherein the Group VIII metal is rhodium.

52. The complex of claim 51 of the formula

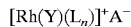

wherein

Y is the optically active compound of formula I;

L is a neutral ligand;

A is the anion of an oxygen acid or complex acid; and n is 0, 1 or 2.

53. The complex of claim 51 of the formula

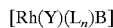

wherein

Y is the optically active compound of formula I;

L is a neutral ligand;

B is an anionic coordinating ligand; and n is 0, 1 or 2.

54. A compound, in racemic or (R)- or (S)-form, of the formula

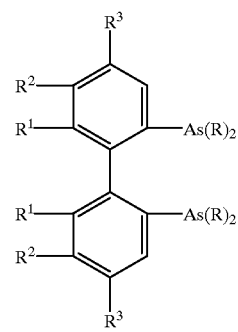

I wherein

R is phenyl, naphthyl, furyl or thienyl, unsubstituted or substituted by one or more groups selected from phenyl, $C_{1-8}$alkyl, $C_{1-8}$-alkoxy, di- $C_{1-6}$-alkylamino, and halogen; or $C_{3-8}$-cycloalkyl or $C_{1-8}$-alkyl; and either $R^1$ and $R^2$ together are dioxymethylene, and $R^3$ is $C_{1-8}$-alkyl, $C_{1-8}$-alkoxy, aryloxy, F, Cl, or hydrogen; or $R^2$ and $R^3$ together are dioxymethylene, and $R^1$ is $C_{1-8}$-alkyl, $C_{1-8}$-alkoxy, aryloxy, F, or Cl.

55. The compound of claim 54, wherein the compound is in the (R)-form.

56. The compound of claim 54, wherein the compound is in the (S)-form.

57. The compound of claim 54, wherein $R^2$ and $R^3$ together are dioxymethylene, and $R^1$ is $C_{1-8}$-alkyl.

58. The compound of claim 54, wherein $R^2$ and $R^3$ together are dioxymethylene, and $R^1$ is methyl.

59. The compound of claim 1, wherein $R^2$ and $R^3$ together are dioxymethylene, and $R^1$ is $C_{1-8}$-alkoxy.

60. The compound of claim 59, wherein $R^1$ is methoxy.

61. The compound of claim 59, wherein $R^1$ and $R^2$ together are dioxymethylene, and $R^3$ is hydrogen.

62. The compound of claim 54, wherein R is unsubstituted phenyl.

63. The compound of claim 54, wherein R is $C_{3-8}$-cycloalkyl.

64. The compound of claim 63, wherein R is cyclohexyl.

65. The compound of claim 54, wherein R is phenyl substituted by $C_{1-8}$-alkyl.

66. The compound of claim wherein R is phenyl para-substituted by $C_{1-8}$-alkyl.

67. The compound of claim 66, wherein R is para-tolyl.

68. A Group VIII metal complex with a compound in optically active (R)- or (S)-form, wherein the compound of the formula

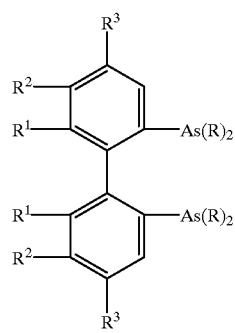

I wherein
  R is phenyl, naphthyl, furyl or thienyl, unsubstituted or substituted by one or more groups selected from phenyl, $C_{1-8}$-alkyl, $C_{1-8}$-alkoxy, di-$C_{1-6}$-alkylamino, and halogen; or $C_{3-8}$-cycloalkyl or $C_{1-8}$-alkyl; and either
  $R^1$ and $R^2$ together are dioxymethylene, and
  $R^3$ is $C_{1-8}$-alkyl, $C_{1-8}$-alkoxy, aryloxy, F, Cl, or hydrogen; or
  $R^2$ and $R^3$ together are dioxymethylene, and
  $R^1$ is $C_{1-8}$-alkyl, $C_{1-8}$-alkoxy, aryloxy, F, or Cl.

69. The complex of claim 68, wherein the Group VIII metal is ruthenium.

70. The complex of claim 68, wherein the Group VIII metal is rhodium.

* * * * *

UNITED STATES PATENT AND TRADEMARK OFFICE
CERTIFICATE OF CORRECTION

PATENT NO. : 6,037,479
DATED : March 14, 2000
INVENTOR(S) : Broger et al.

It is certified that error appears in the above-identified patent and that said Letters Patent is hereby corrected as shown below:

Title page, [73], Assignee: "Hoffman-La Roche Inc., Nytley, N.J." should be

-- Hoffmann-La Roche Inc., Nutley, N.J. --.

Column 11, claim 49, line 62, "$Ru(Y)(B)2]$" should be -- $[Ru(Y)(B)_2]$ --.

Column 12, claim 52, line 24, "A" should be -- $A^-$ --.

Signed and Sealed this

Thirteenth Day of March, 2001

Attest:

NICHOLAS P. GODICI

Attesting Officer

Acting Director of the United States Patent and Trademark Office